(12) United States Patent
Martin et al.

(10) Patent No.: US 7,700,348 B2
(45) Date of Patent: Apr. 20, 2010

(54) BIOCHIP AND THE PRODUCTION METHOD THEREOF

(75) Inventors: Jean René Martin, Lozanne (FR); Michel Garrigues, La Tour de Salvagny (FR); Marlène Bras, Tassin la Demi Lune (FR); Francois Bessueille, Georges (FR); Eliane Souteyrand, Celletes (FR); Michel Cabrera, Lyons (FR); Jean-Pierre Cloarec, Lyons (FR); Jean-Paul Chauvet, Saint Didier au Mont d'OR (FR); Dorothée Chauvet, legal representative, Elancourt (FR); Jean-Michel Chauvet, legal representative, Saint-Denis (FR); Christophe Chauvet, legal representative, Elancourt (FR)

(73) Assignees: Centre National de la Recherche Scientifique, Paris (FR); Ecole Centrale de Lyon, Ecully (FR)

( * ) Notice: Subject to any disclaimer, the term of this patent is extended or adjusted under 35 U.S.C. 154(b) by 587 days.

(21) Appl. No.: 10/483,379

(22) PCT Filed: Jul. 5, 2002

(86) PCT No.: PCT/FR02/02365

§ 371 (c)(1), (2), (4) Date: Jul. 21, 2004

(87) PCT Pub. No.: WO03/008975

PCT Pub. Date: Jan. 30, 2003

(65) Prior Publication Data

US 2004/0248122 A1 Dec. 9, 2004

(30) Foreign Application Priority Data

Jul. 11, 2001 (FR) .................... 01 09245

(51) Int. Cl.
*C12M 1/34* (2006.01)
(52) U.S. Cl. .................. 435/288.7; 435/283.1; 356/36; 356/38; 356/450; 436/518; 436/527
(58) Field of Classification Search ............... 435/7.22; 422/82.01, 82.02
See application file for complete search history.

(56) References Cited

U.S. PATENT DOCUMENTS 4,882,288 A 11/1989 North et al. .............. 436/525
5,156,810 A * 10/1992 Ribi ..................... 422/82.01

(Continued)

FOREIGN PATENT DOCUMENTS

WO 96/26432 8/1996

(Continued)

*Primary Examiner*—N. Yang
(74) *Attorney, Agent, or Firm*—Morgan, Lewis & Bockius LLP

(57) ABSTRACT

The invention relates to a biochip comprising a substrate presenting a reflecting main surface and wherein the main surface presents localized sites that are made sensitive to fluorescence detection by a transparent layer having optical thickness $(2k+1)\lambda/4$ where k is a positive or zero integer and where $\lambda$ designates a wavelength lying between a wavelength $\lambda_0$ at which fluorescence is excited and a wavelength $\lambda_1$ at which fluorescence is emitted. The biochip can be manufactured by depositing a transparent layer of thickness $m\lambda'/2$ on a substrate and by making studs or wells of thickness $(2k+1)\lambda/4$ in said layer to form said sensitive sites.

20 Claims, 1 Drawing Sheet

U.S. PATENT DOCUMENTS

| | | | | |
|---|---|---|---|---|
| 5,541,057 A | * | 7/1996 | Bogart et al. | 435/5 |
| 5,812,272 A | | 9/1998 | King et al. | 356/445 |
| 5,866,433 A | | 2/1999 | Schalkhammer et al. | 436/525 |
| 6,008,892 A | * | 12/1999 | Kain et al. | 356/246 |
| 2003/0148304 A1 | * | 8/2003 | Liang et al. | 435/6 |

FOREIGN PATENT DOCUMENTS

WO  99/45354  9/1999

* cited by examiner

BIOCHIP AND THE PRODUCTION METHOD THEREOF

The present invention relates to a biochip of the type enabling biological or biochemical probes to be detected by fluorescence, and the invention also relates to a method of manufacturing it.

BACKGROUND OF THE INVENTION

Biochips are very high performance analysis tools in fields relating to molecular biology. The technology for preparing them is in the process of becoming established. Their use will enable research to be accelerated and will lead, in particular, to new diagnostic techniques.

A biochip is a set of systems of biological recognition substances such as biological molecules, all operating in parallel. Amongst biochips, those which have been developed to the greatest extent so far are DNA chips and there are great hopes that they will enable recognition efforts to be greatly increase in the field of molecular genetics.

Physically, biochips are structures constituted by a solid support having distinct zones distributed thereon, in general of microscopic dimensions, and supporting identical biological recognition probe substances, each zone or site having a single type of substance which may be of biological or biochemical origin. Recognition is performed by a specific affinity interaction between the probe substance fixed on the support and the target substance contained in the solution to be analyzed. The biochip is read by marking the target substance using a marker, generally a fluorescent marker. During recognition, the target substance brings its marker to the zone that supports the probe substance. Knowing the nature of the probe makes it possible to know the target substance with which the affinity reaction has taken place.

OBJECTS AND SUMMARY OF THE INVENTION

The invention seeks firstly to improve the technical quality of the biochip, and secondly to improve the quality with which the fluorescence can be read.

The fixing of molecules such as oligonucleotides or strands of DNA on the support in order to make the biochip relies on chemical reactions that take place at the surface of the solid. Usually, the probe biological molecule for fixing is in solution. Depending on the relative surface properties of the support and of the solution containing the probes to be fixed, the deposited solution may tend to spread out over the substrate, making it impossible to obtain zones of interest that are of controlled size and small dimensions.

Similarly, direct localized synthesis of biological molecules such as oligonucleotides can be performed by localized deposition on the surface of the substrate of a portion of the reagents, and in particular phosphoramidites. These various reagents are usually in solution in a solvent such as acetonitrile. This solvent has the property of being highly wetting, which means that if the necessary precautions are not taken it causes the reagents to be spread over the surface. Thus, these properties prevent the area on which synthesis takes place to be controlled and thus prevents the zones of interest from being defined geometrically.

In addition, analysis is performed by putting the biochip into contact with a solution containing the target molecules which are marked before or after contact with a fluorescent group (or possibly they are marked in radioactive manner). Recognition is the result of relatively strong biochemical coupling between the probe and the analyte (e.g. by forming hydrogen bonds). The analyte is thus fixed on the recognition area and can be identified by knowledge of the probe that is coupled or secured to said area or site.

In parallel with this specific recognition, depending on the nature of the support, target molecules can also become fixed in non-selective manner thereon (usually by an adsorption process). This parasitic phenomenon has the effect of reducing the signal-to-noise ratio when reading.

An object of the present invention is to provide a solution to those problems in order to improve the biological quality of the chip by acting on its optical quality.

In addition, in an advantageous variant, the improvement in the physicochemical quality of the chip by localized double functionalization can enable the site supporting the biological probe molecules to be better defined geometrically while still ensuring that all of the sites are identical in size and are in alignment, and while considerably reducing non-selective adsorption of target molecules.

The invention thus provides a biochip comprising a substrate presenting a reflecting main surface, wherein the main surface presents localized sites that are made sensitive to fluorescence detection by a transparent layer having optical thickness $(2k+1)\lambda/4$ where k is a positive or zero integer and where $\lambda$ designates a wavelength lying in the range from a wavelength $\lambda_0$ at which fluorescence is excited and to a wavelength $\lambda_1$ at which fluorescence is emitted. The term "optical thickness" is used to mean the product of the actual physical thickness multiplied by the refractive index of the transparent layer.

In the biochip, the main surface presents sites that have been made sensitive to fluorescence detection by a transparent layer of optical thickness equal to $(2k+1)\lambda_1/4$ where k is a positive integer or zero, thereby enhancing fluorescent emission.

In the biochip, outside the sensitive sites, the main surface is covered in a transparent layer of thickness $m\lambda'/2$ where m is a positive integer or zero and $\lambda'$ designates a wavelength lying in the range $\lambda_o$ to $\lambda_1$.

Preferably, outside the sensitive sites, the main surface is covered in a transparent layer of thickness $m\lambda_0/2$, thus serving to prevent fluorescence being excited.

In an advantageous embodiment that makes use of localized silanization, and outside the sensitive sites, the surface of the substrate is covered in a first thin layer, in particular a monolayer of molecules of a first substance A, comprising a hydrocarbon chain of the $(CH_2)p$ type with $1<p<30$ carrying a catching-hold group such as a silane or a silanol at one end enabling a covalent bond to be made, and carrying a chemical function at its other end that is stable and inert, e.g. $CH_3$ and halogenated derivatives thereof. Said first substance is hydrophobic.

In a preferred embodiment, the sensitive sites are covered in a second thin layer, in particular a monolayer of molecules of a second substance B presenting a group at one end suitable for fixing to the substrate by means of a covalent bond, e.g. a silane function or a silanol function, and presenting a group at its other end suitable for fixing in covalent manner to a probe molecule, e.g. a group presenting the acid COOH function or the alcohol OH function.

Said second substance is hydrophilic.

In the biochip, the surface of the substrate is covered in a layer of said substance B, and outside the sensitive sites, said layer is covered in a stop layer C.

The invention also provides a method of manufacturing a biochip as defined above, the method implementing the following steps:

a) depositing a transparent layer of thickness $m\lambda'/2$ on a substrate; and b) making wells or studs in said transparent layer in which the thickness of the transparent layer is equal to $(2k+1)\lambda/4$, so as to form said sensitive sites.

Depending on the values of k and m, it is possible to make sensitive sites that are in the form of wells or of studs.

When the sensitive zones are wells, the method may implement the following steps:

c) localized double silanization by selectively depositing said first thin layer, said deposition optionally being followed by heat treatment; and d) immersing the substrate in a solution containing the second substance B.

When the sensitive zones are studs, the method implements the following steps:

c') localized double silanization by selectively depositing substance B on the studs, said deposition optionally being followed by heat treatment; and d') immersing the support in a solution containing the substance A.

In another embodiment, the localized double silanization is performed as follows (after b):

e) a layer of substance B is deposited over the entire surface of the substrate, e.g. by immersion in the solution containing substance B. The function for fixing the probe substance is then deprotected and activated.

f) A monolayer of molecules of a stop substance C is then locally deposited on the surface in such a manner as to leave the sensitive zones 5 bare. The molecules of the substance C have at one end a function which reacts with the activated function of the substance B. The other end of the molecule has a group that is highly inert chemically, such as a methyl group or indeed a fluorine-substituted methyl group. Thus, only activated sensitive zones are suitable for fixing the probe substances, the outside surfaces of the sensitive zones being made definitively inert against catching hold of biological substances.

Between the functional groups of the molecule of the substance C, there may exist an organic chain such as an aliphatic chain of the $(CH_2)q$ type where $0 < q < 30$.

It is important to observe that the functionalization layers are of thicknesses of the order of 1 nanometer (nm) to 10 nm and therefore possess optical thickness that is negligible compared with the transparent layer and thus has no direct action on the optical properties of the biochip.

Optionally, steps c) and/or d), and/or e), and/or f), and/or g), and/or h) may be followed by heat treatment for facilitating silanization.

BRIEF DESCRIPTION OF THE DRAWINGS

Other characteristics and advantages of the invention will appear better on reading the following description given with reference to the accompanying drawing in which.

MORE DETAILED DESCRIPTION

U.S. Pat. No. 6,008,892 describes a structure that takes advantage of the optical properties of thin plates: when a transparent layer of optical thickness equal to one-fourth of the wavelength or an odd multiple of one-fourth of the wavelength lies on a reflecting (or partially reflecting) substrate, then light emitted by a fluorescent source emitting at this wavelength is at a maximum. In that method, the entire surface of the substrate is treated uniformly so as to increase emission by fluorescence. Parasitic fluorescence due to biological substances adsorbed outside the sensitive zones is thus improved in the same manner as the fluorescence in the sensitive zones, thereby achieving no improvement in the signal-to-noise ratio between the sensitive zones and the non-sensitive zones.

The present invention remedies that drawback by structuring the thickness of the transparent layer of the substrate, thereby enabling the fluorescence of sensitive zones to be improved while on the contrary inhibiting fluorescence outside the sensitive zones.

Figure 1A:
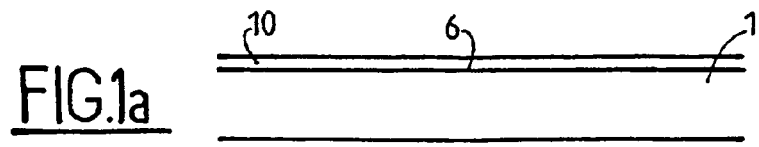
FIGS. 1a to 1e show a first embodiment of the method of manufacture. A preferred embodiment is shown in FIGS. 1a to 1d and in FIGS. 2a to 2c. A variant is shown in FIG. 3.
Figure 1B:
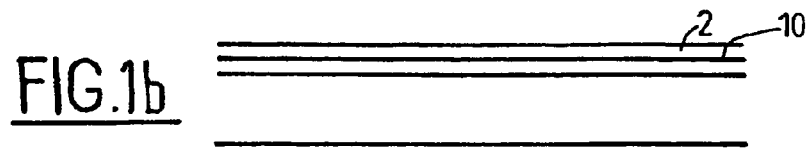
Figure 1C:
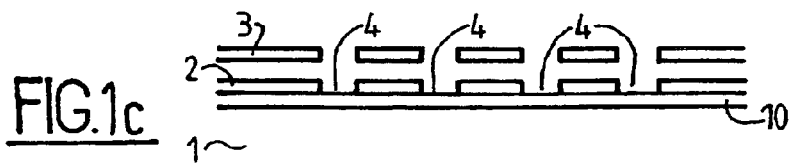
Figure 1D:
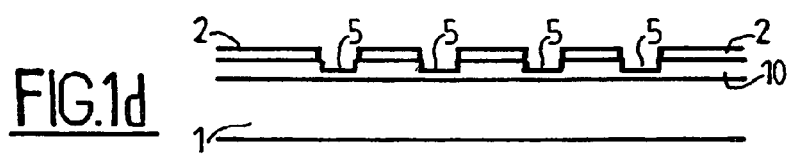

In the invention, the optimized structure is made from a layer 10 having an optical thickness $\lambda/2$ (or more generally $m\lambda/2$), being made of a transparent material deposited on the surface 6 of a substrate 1 that reflects at the reading wavelength, for example a layer 10 of silica or of silicon nitride on a silicon substrate, or a layer of metallic oxide on a metal substrate, e.g. $TiO_2$ on titanium, $ZrO_2$ on zirconium, etc. (FIG. 1a). A film 7 of photosensitive resin is deposited on this layer 10 (FIG. 1b). The resin is exposed through a mask 3 which enables opening 4 to be opened in the resin 2 after it has been developed, the openings serving to form sensitive sites on the chip (FIG. 1c). Chemical etching is then performed to reach an optical thickness for the film that is equal to $(2k+1)\lambda/4$ (FIG. 1d) in the localized zones 12 so as to form wells 5 constituting the sensitive sites of the chip.

Preferably, the emission of fluorescence in the sensitive sites is enhanced by selecting a transparent layer of optical thickness $(2k+1)\lambda_1/4$. Excitation of fluorescence is preferentially inhibited outside the sensitive sites by selecting a transparent layer having an optical thickness of $m\lambda_0/2$.

Figure 1E:
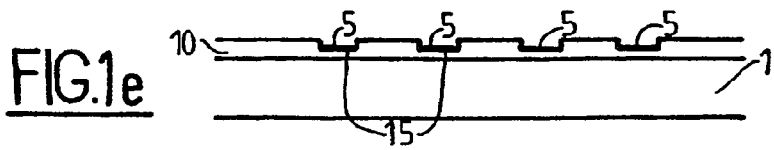

After the resin 2 has been eliminated, a film of a silane 15 having at its end a functional group suitable for immobilizing the biological molecule can advantageously be deposited in the wells 5 (FIG. 1e). The structure is then raised in temperature in order to enhance the silanization reaction. The thickness of this thin layer (generally monomolecular) does not significantly change the optical properties of the structure.

Thereafter, probe biological molecules are fixed on the various sensitive sites by ex situ or in situ techniques. The free top surface of the layer is subjected finally to treatment having the effect of neutralizing the active functional groups that have not reacted during the preceding stage. If molecules should nevertheless become fixed outside the sensitive zone by the deposition solution overflowing, for example, then the fluorescence signal outside the sensitive zone is weaker by a factor of about 200 than the signal coming from within the sensitive zone and, in most cases, it will have no effect on reading.

Thus, the optical path difference between the inside and the outside of the wells improves the signal-to-noise ratio when reading fluorescence by minimizing the fluorescence signal outside the wells and by optimizing the fluorescence signal inside the wells.

It is possible to improve both the biochip by simultaneously improving both the optical quality and the physicochemical quality of the substrate.

The substrate is micromachined by chemical etching so as to make the sensitive sites in the layer as described above (FIGS. 1a to 1d). A transfer operation is then performed.

Figure 2A:
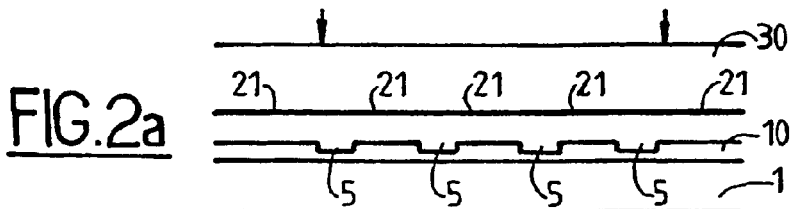
Figure 2B:
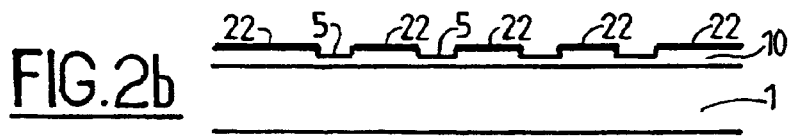
Figure 2C:
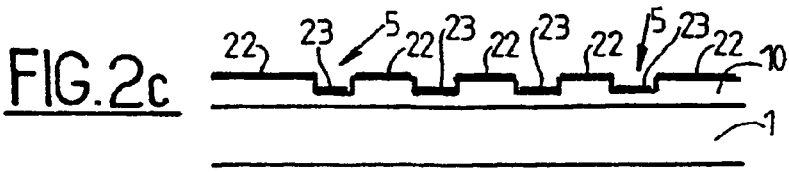

After chemical etching and eliminating the resin (FIG. 1d), the chip is put into contact with a transfer surface 30 having a fine layer 21 of a solvent deposited thereon, the solvent containing a substance of type A, e.g. a hydrophobic silane (FIG. 2a). The hydrophobic silane is thus transferred onto the top surface of the chip as to form a thin layer 22 (FIG. 2b). Silane can also be deposited by an inking device using the silane-containing solution. Heat treatment encourages the silanization reaction to take place on the surface of the chip. A second silanization step is undertaken, for example by dipping the chip in a solution containing the second silane, and serves to silanize a thin layer 23 on the bottoms of the initially bare wells (the second silane does not fix to the first) (FIG. 2c). The specific second silane has at its free end a functional group of a kind that is known per se and that makes it possible either to achieve a covalent bond with the biological substance in order to hold said biological substance in place, or else to start in situ synthesis of the probe biological molecule: this starting reaction also corresponds to establishing a covalent bond.

The thickness of the thin layers 22 and 23 (no more than a few layers of molecules) is not sufficient to modify significantly the optical properties of the surface, which thus combines the selective properties obtained by the two techniques.

The method thus makes use of physicochemical confinement. It consists in defining zones that are to receive probes of a hydrophilic nature, by locally using microtransfer to deposit molecules for forming a hydrophobic monolayer in the region between the sensitive sites. The insides of the sensitive sites are then silanized using a silane suitable for holding onto previously synthesized probes or for in situ synthesis of biological molecules. The microtransfer of the hydrophobic monolayer is performed by using a transfer surface 30 which may be plane, or which may be constituted by a micropad presenting transfer regions in relief.

The transfer surface 30 is put into contact with a solution containing the hydrophobic silane. A fine film 22 of solution is then transferred by contact at localized positions on the layer 10 of the substrate 1. The substrate 1 is then raised to a temperature of about 100° C. in order to facilitate the silanization reaction. By using a specific protocol and selecting an appropriate molecule, it is possible to obtain a monolayer that is organized and compact, known as a self-assembled monolayer (SAM). Zones that have not received the silane are then treated so as to be covered in another silane whose free end possesses a functional group that enables in situ synthesis of oligonucleotides to be performed (e.g. a hydroxyl group, or that enables biological molecules that have been presynthesized or that are of biological origin to be held in place by using an appropriate functional group (e.g. an acid). The grafting reaction of the second silane takes place on the silanol groups of the silica or the glass constituting the substrate but it cannot take place on the monolayer of the fixed first silane. Thus, only those zones that are to act as sensitive sites are functionalized.

In addition, the hydrophobic silane limits non-selective adsorption very strongly, and as a result very significantly improves the signal-to-noise ratio when reading by fluorescence (or possibly by radioactive marker), by increasing the ratio of the true signal in zones supporting biological probes to any signal that might come from bare zones where non-selective adsorption might have occurred.

In general, it is possible to perform the same function using substances other than silane.

It is possible to deposit a physically and chemically inert layer on the top portion of the support outside the sensitive site, thereby limiting adsorption and fixing of probe biomolecules while making biochips and limiting the adsorption or fixing of target biomolecules during biological analysis, thereby improving the measurement signal-to-noise ratio.

This inert layer is constituted by a molecule comprising a hydrocarbon chain of the $(CH_2)p$ type with $1<p<30$ or a polymer chain, e.g. poly-ethylene-glycol, etc. or an assembly of various chain portions, carrying at one end a group that enables a covalent bond to be formed with the support, e.g. a silane or a silanol bond, while the other end carries a chemical function that is stable and inert such as $CH_3$ or its halogenated derivatives substituting all or some of the hydrogens in the aliphatic chain $(CH_2)p$ and the $CH_3$. The layer that is formed may be monomolecular or polymeric depending on the nature of the first terminal group. The layer may advantageously be deposited by contact with a plane surface previously covered in a solution of said molecule.

Thereafter a monolayer of molecules presenting different functions at each end should be deposited on the sensitive sites: one serves to fix the molecule by a covalent bond on the substrate, e.g. a silanol function, and the other serves to fix the probe biomolecule in covalent manner, e.g. the acid function COOH or an alcohol function OH. This monolayer then serves to hold biomolecules that have been presynthesized or that are of natural origin, or indeed it enables the probe biomolecules (oligonucleotides, PNA, protein, etc.) to be synthesized in situ in the wells.

Figure 3:
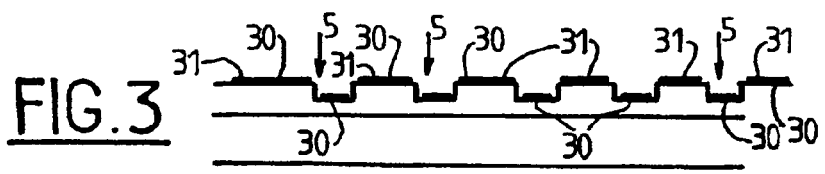

Another method is described with reference to FIG. 3.

The surface of the substrate is covered in a layer 30 of the substance B, then a layer 31 of the stop substance C is deposited locally outside the sensitive site, in this case the wells 5.

Preferably, the sensitive sites are made to be effective in detection by using two techniques that have complementary effects: the physical effect associated with the difference in height between the insides of the sites and the outside, and the physicochemical effect associated with the surface property differences between the insides of the sites and the outside. As a result, the shape and the relative position of the sensitive sites obtained by a microtechnological type technique are well defined. This contributes to obtaining a high quality chip and improving the reading thereof.

Finally, by associating two techniques, three-dimensionally structuring the support and preparing its surface to enable attachment to take place in preferred manner in the sensitive sites, e.g. by double silanization, it is possible to improve the quality of the chip and to optimize reading thereof by acting on four aspects which can be implemented separately or together:

improving the geometrical definition of the chip by using masking and/or transfer techniques;

decreasing the size of the sensitive sites by the combined effects of the physicochemical confinement and the machining of the sites;

decreasing non-specific adsorption on the zone between the sites by depositing a monolayer of hydrophobic silane by microtransfer, for example; and improving the optical quality with which the chip is read by optimizing the thicknesses of the transparent support layer.

What is claimed is:

1. A biochip comprising a substrate containing a reflecting main surface, wherein the main surface presents localized sites covered by a transparent layer to enhance fluorescence, whereby the sites are made sensitive to fluorescence detection of fluorescent light emitted by target molecules marked by a fluorescent material that is deposited over the transparent layer, wherein the transparent layer has an optical thickness of $(2k+1)\lambda/4$ where k is a positive integer or zero and where $\lambda$ designates a wavelength lying in the range from a wavelength $\lambda_0$ at which fluorescence of the fluorescent material is excited to a wavelength $\lambda_1$ at which the fluorescence of the fluorescent material is emitted, and further wherein, outside the sensitive sites, the main surface of the substrate is covered in a transparent layer of thickness different than that of the transparent layer of the sensitive sites, the thickness outside the sensitive sites being of $m\lambda'/2$ where m is a positive integer and $\lambda'$ designates a wavelength lying in the range $\lambda_0$ to $\lambda_1$.

2. A biochip according to claim 1, wherein the transparent layer covering the sites has an optical thickness equal to $(2k+1)\lambda_1/4$ where k is a positive integer.

3. A biochip according to claim 1, wherein, outside the sensitive sites, the main surface of the substrate is covered in a transparent layer of thickness $m\lambda'/2$ where m is a positive integer and $\lambda'$ designates a wavelength lying in the range $\lambda_o$ to $\lambda_1$.

4. A biochip according to claim 3, wherein, outside the sensitive sites, the main surface of the substrate is covered in a transparent layer of thickness $m\lambda_1/2$.

5. A biochip according to claim 1, wherein, outside the sensitive sites, the surface of the substrate is covered in a thin layer of molecules of a first substance A comprising a hydrocarbon chain of the $(CH_2)p$ type with $1<p<30$ carrying a catching-hold group at one end enabling a covalent bond to be made with the substrate, and carrying a chemical functional group at its other end that is stable and inert.

6. A biochip according to claim 5, wherein the thin layer of molecules of a first substance A is a monolayer of molecules.

7. A biochip according to claim 5, wherein the catching-hold group is a silane or a silanol.

8. A biochip according to claim 5, wherein the chemical functional group is $CH_3$ or halogenated derivatives of $CH_3$.

9. A biochip according to claim 7, wherein the first substance comprises a hydrophobic silane.

10. A biochip according to claim 1, wherein the sensitive sites are covered in a thin layer of molecules of a second substance B presenting a group at one end suitable for fixing to the substrate by means of a covalent bond and presenting a group at its other end suitable for fixing in covalent manner to a probe molecule.

11. A biochip according to claim 10, wherein the thin layer of a second substance B is a monolayer of molecules.

12. A biochip according to claim 10, wherein the group suitable for fixing to the substrate by means of a covalent bond is a silane functional group or a silanol functional group.

13. A biochip according to claim 10, wherein the group suitable for fixing to a probe molecule is a group presenting an acid COOH functional group or an alcohol OH functional group.

14. A biochip according to claim 12, wherein said second substance is a hydrophilic silane.

15. A biochip according to claim 10, wherein the surface of the substrate is covered in a layer of said second substance B, and wherein, outside the sensitive sites, said layer of said second substance B is covered in a stop substance C.

16. A method of manufacturing the biochip of claim 1, the method comprising the following steps:
   a) depositing a transparent layer of thickness $m\lambda'/2$ on a substrate, where m is a positive integer or zero and $\lambda'$ designates a wavelength lying in the range $\lambda_0$ to $\lambda_1$; and
   b) making wells or studs in said transparent layer in which the thickness of the transparent layer is equal to $(2k+1)\lambda/4$, where k is a positive integer or zero and where $\lambda$ designates a wavelength lying in the range from a wavelength $\lambda_0$ at which fluorescence is excited and to a wavelength $\lambda_1$ at which fluorescence is emitted, so as to form said sensitive sites.

17. A method according to claim 16, further comprising the following steps:
   c) depositing said first thin layer of a first substance A comprising a hydrocarbon chain of the $(CH_2)p$ type with $1<p<30$ carrying a catching-hold group at one end enabling a covalent bond to be made with the substrate, and carrying a chemical functional group at its other end that is stable and inert by selective transfer onto the substrate; and
   d) immersing the substrate in a solution containing a second substance B presenting a group at one end suitable for fixing to the substrate by means of a covalent bond and presenting a group at its other end suitable for fixing in covalent manner to a probe molecule.

18. A method according to claim 17, wherein step c) and/or d) is followed by heating the substrate to a temperature effective to facilitate the formation of a covalent bond.

19. A method according to claim 16, wherein, after step b), the method further comprises the following steps:
   c) depositing a thin layer of a substance B presenting a group at one end suitable for fixing to the substrate by means of a covalent bond and presenting a group at its other end suitable for fixing in covalent manner to a probe molecule, over the entire surface of the substrate; and
   d) depositing a layer of a stop substance C outside said sensitive sites.

20. A biochip according to claim 1, wherein k is zero and, outside the sensitive sites, the main surface of the substrate is covered in a transparent layer of thickness $m\lambda'/2$ where m is a positive integer and $\lambda'$ designates a wavelength lying in the range $\lambda_0$ to $\lambda_1$.

* * * * *